US009192319B2

(12) United States Patent
Hou et al.

(10) Patent No.: US 9,192,319 B2
(45) Date of Patent: Nov. 24, 2015

(54) METHOD FOR SEPARATING SIGNAL SOURCES BY USE OF PHYSICALLY UNIQUE DICTIONARY ELEMENTS

(75) Inventors: Jidong Hou, Eugene, OR (US); Don M. Tucker, Eugene, OR (US)

(73) Assignee: Electrical Geodesics, Inc., Eugene, OR (US)

( * ) Notice: Subject to any disclaimer, the term of this patent is extended or adjusted under 35 U.S.C. 154(b) by 460 days.

(21) Appl. No.: 13/549,242

(22) Filed: Jul. 13, 2012

(65) Prior Publication Data

US 2014/0018693 A1 Jan. 16, 2014

(51) Int. Cl.
*A61B 5/04* (2006.01)
*H03F 1/26* (2006.01)
*A61B 5/0476* (2006.01)

(52) U.S. Cl.
CPC .................................. *A61B 5/0476* (2013.01)

(58) Field of Classification Search
CPC .............................. G06K 9/624; G06K 9/6244
USPC .................. 600/544, 545; 702/190, 191, 196
See application file for complete search history.

(56) References Cited

U.S. PATENT DOCUMENTS

| 6,845,164 | B2* | 1/2005 | Gustafsson | 381/94.1 |
| 7,647,209 | B2* | 1/2010 | Sawada et al. | 702/190 |
| 2005/0149462 | A1* | 7/2005 | Lee et al. | 706/20 |
| 2006/0036926 | A1* | 2/2006 | Hocevar | 714/758 |
| 2006/0066482 | A1* | 3/2006 | Goldberg | 342/378 |
| 2010/0217145 | A1* | 8/2010 | Buscema | 600/544 |
| 2010/0286963 | A1* | 11/2010 | Souloumiac | 702/196 |

OTHER PUBLICATIONS

Bruno A. Olshausen and David J. Field, Sparse Coding with an Overcomplete Basis Set: A Strategy Employed by VI? Vision Res., vol. 37 No. 23; pp. 3311-3325, Elsevier Science 1997.
Ivana Tosic, and Pascal Frossard, "Dictionary Learning [What is the right representation for my signal?]," IEEE Signal Proc. Magazine Mar. 2011, published Feb. 17, 2011.

* cited by examiner

*Primary Examiner* — Etsub Berhanu
(74) *Attorney, Agent, or Firm* — Portland Intellectual Property, LLC

(57) ABSTRACT

A method for separating signal sources by use of physically unique dictionary elements. The method is particularly advantageous for separating cerebral from artifactual sources in electroencephalographic (EEG) recording, making use of dictionary element pattern recognition methods that are tuned to the unique physical properties of each source domain.

10 Claims, 5 Drawing Sheets

METHOD FOR SEPARATING SIGNAL SOURCES BY USE OF PHYSICALLY UNIQUE DICTIONARY ELEMENTS

FIELD OF THE INVENTION

The present invention relates to a method for separating cerebral from artifactual sources in electroencephalographic (EEG) recording, by use of dictionary element pattern recognition methods that are tuned to the unique physical properties of each source domain.

BACKGROUND

EEG ("electroencephalography") signal data are often obtained for the purpose of identifying where, in the brain, the sources of neuronal activity are located. The data are collected from a network of spaced-apart electrical sensors worn on the head surface, each sensor sensing the electrical potential produced at its particular location. The electrical potentials are resulting effects of the neuronal activity. It is desired to solve for the distribution of the sources.

The straightforward, "forward conduction" problem, is to solve for the electrical potentials knowing the sources. That is, $$\begin{bmatrix} \Phi_1 \\ \Phi_2 \\ \vdots \\ \Phi_{Ne} \end{bmatrix} = \begin{bmatrix} K_{1,1} & K_{1,2} & \cdots & K_{1,Nd} \\ K_{2,1} & K_{2,2} & \cdots & K_{2,Nd} \\ \cdots \\ K_{Ne,1} & K_{Ne,2} & \cdots & K_{Ne,Nd} \end{bmatrix} \begin{bmatrix} J_1 \\ J_2 \\ \vdots \\ J_{Nd} \end{bmatrix}$$

or, $$\Phi = KJ$$

where $\Phi_i$ is the measured electrical potential at a particular sensor "i" (i ranging from 1 to Ne); $J_k$ is the neuronal activity of a particular source "k" (k ranging from 1 to Nd); and K is the "lead forward" matrix.

It is less straightforward to solve the "inverse problem," i.e., to solve for the source locations knowing the electrical potentials. Even if the matrix K is square, one cannot generally simply invert it to solve for J, because the sensor data are not independent. The data are generally insufficient to specify a unique solution, and the inverse problem is typically treated as an optimization problem, with the permitted solutions being subject to anatomical or other constraints.

It is particularly important for solving the inverse problem to ensure that the measured potentials result solely from the neuronal source activity. If the measured potentials have other causes, it is not possible to solve the inverse problem accurately, and the measured potentials typically do have other causes. For example, the electrical activity associated with blinking an eye will contribute to the measured electrical potentials. The sensors, particularly by virtue of the lead wires acting as antennas, will also pick up electrical noise from the environment. These and other additional sources of electrical potential generate "artifacts" in the measured signal.

A specific artifactual problem occurs when BEG is conducted during MRI, when the electrodes are disposed in a very strong magnetic field. A "ballistocardiographic" artifact (BCGa) results from pulsating blood flows in the arteries in the scalp causing electrode movement, which generates an electrical potential in the magnetic field that is of considerably larger magnitude than the electrical potential resulting from the neuronal sources.

The standard approach for removing artifacts produced by causes such as eye-blinks from EEG data is to use techniques like statistical decomposition, principle component analysis (PCA), or independent component analysis (ICA), to find components of the measured signal that are characteristic of such causes to identify components that are subtracted from the signal. Then, the source analysis (solving the inverse problem) is performed on the remaining signal.

These techniques are not completely effective and there remains a need for further improvement.

SUMMARY

Disclosed is a method for separating signal sources by use of physically unique dictionary elements. It is desired to separate from a total signal, two signal components of the total signal resulting from two respective signal sources of physical activity, where the two signal sources are of two distinct types. The signal sources of one of the types are spatially separated from the signal sources of the other of the types with a result being that the signals of the two types propagate through distinctly different conductive paths and thereby have distinctly different spatial frequencies. The method includes measuring the total signal at one or more locations; and simultaneously separating the two signal components. The separation methodology includes forming a first plurality of templates corresponding to one of the signal components, forming a second plurality of templates corresponding to the other signal component, combining the first and second pluralities of templates in a matrix, solving for a vector relating the total signal to the sources of both types by use of the matrix, the vector thereby defining coefficients corresponding to both signal components, and computing one of the two signal components by use of the matrix and vector, including nullifying at least one of (a) the elements of the vector, and (b) the templates in the matrix, corresponding to the other signal.

Preferably, the signal sources of the first type are neurons located inside the skull of an animal and the signal sources of the second type are located outside said skull; more preferably, the method further includes disposing, outside the skull, an array of spaced-apart electrical sensors, and the step of measuring includes receiving electrical outputs produced by the sensors; and more preferably still, the sensors are disposed on the surface of the head of the animal.

Preferably as well, the method further includes ensuring that the number of templates in the matrix is greater than the number of locations where the measurements of the total signal were, are being, or will be made, and the step of solving includes imposing a constraint that prefers solutions tending to maximize the sparseness of the coefficients.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DETAILED DESCRIPTION OF PREFERRED EMBODIMENTS

The present invention provides a novel application of the methodology known as "sparse coding" to the problem of artifact removal from EEG signals.

Sparse Coding

Neurons communicate with each other by sending and receiving electrical pulses that encode sensory (input) or command (output) information. It is an important aspect of neuroscience to study how information is coded in these pulses, referred to as "neural coding."

It is not yet fully understood how neural information is actually coded, so various "coding schemes" are used as assumptions. Under a "rate coding" scheme, information is assumed to be specified in an average firing rate of a neuron. Under a "temporal coding" scheme, information is assumed to be specified in details of the timing of the firing of the neuron that cannot be specified as a simple average, such as delay in response to a stimulus, randomness, and timing between groups of pulses. Under a "population coding" scheme, information is assumed to be specified in the aggregate firings within a population of neurons.

"Sparse coding" is another type of neural coding scheme which assumes that, for any particular result of neural activity (e.g., moving a finger), the information is most strongly coded in the activities of a relatively small set of neurons, with the large majority of the neurons not being significantly involved. For example, Olshausen and Field (B. A. Olshausen and D. J. Field, "Sparse coding with an overcomplete basis set: A strategy employed by VI?" Vis. Res., vol. 37, no. 23, pp 3311-25, 1997) have shown that the visual cortex reduces the dimensionality of a retinal image into a space defined by the receptive fields of a small number of active neurons.

The general problem to which sparse coding has been found to be useful as explained by Tošíc and Frossard (I. Tošíc and P. Frossard, "Dictionary Learning: What is the right representation for my signal?" IEE Signal Processing Magazine, pp. 27-38, March 2011), is that much recorded data is largely redundant, both because it often contains multiple, correlated versions of the same physical reality and because each version is densely sampled. So, the relevant information is generally of much reduced dimensionality compared to the recorded data and it is helpful for understanding to reduce the dimensionality of the recorded data as well.

Tošíc and Frossard advocate the use of sparse coding for this purpose, to represent the measured data in reduced dimensionality sub-spaces, based on the principle that the data can be described by a sparse subset of elements, which are typically "unit norm functions" referred to as "atoms," taken from a resource database called a "dictionary."

That is, $$y = [\Phi_1 \ \Phi_2 \ \ldots \ \Phi_N] \begin{bmatrix} a_1 \\ a_2 \\ \vdots \\ a_N \end{bmatrix}$$

or, $$y = \Phi a,$$

where y is a measured signal; $\Phi$ is the dictionary, with each $\Phi_k$ (k ranging from 1 to N) defining an "atom;" and a is the signal representation, the coefficients $a_k$ specifying an appropriate linear combination of the atoms.

For the purpose of sparse coding, the dictionary is designed to be "overcomplete," meaning that if the signal y has a dimension "n," N>n. Then, the objective is to achieve "efficient and sparse representations a," particularly a "sparse vector" a that contains a small number of significant coefficients $a_k$, while the rest of the coefficients are "close or equal to zero." This strategy minimizes the atoms, or "resources," needed to represent the signal.

Finding the sparse vector a is an optimization problem, specifically to find a sparse linear expansion with an approximation error $\eta$ of bounded energy $\epsilon$, a problem which may be formulated as follows:

$$\min_a \|a\|_0 \text{ subject to } y = \Phi a + \eta \text{ and } \|\eta\|_2^2 < \epsilon$$

where $\|\cdot\|_p$ denotes the $I_p$ norm.

This problem is known as being "NP-hard," but Tošíc and Frossard cite in the literature a number of polynomial time approximation algorithms that find a sub-optimal but satisfactory solution for the sparse vector a. These are: (1) matching pursuit (described in S. G. Malla and Z. Zhang, "Matching pursuits with time-frequency dictionaries," IEEE Trans. Signal Process., vol. 41, no. 12, pp. 3397-3415, 1993); (2) orthogonal matching pursuit (described in J. Tropp, "Greed is good: Algorithmic results for sparse approximation," IEEE Trans. Inform. Theory, vol. 50, no. 10, pp. 2231-42, 2004); (3) basis pursuit de-noising (described in S. Chen, D. Donoho, and M. Saunders, "Atomic decomposition by basis pursuit," SIAM J. Sci. Comput., vol. 20, no. 1, pp. 33-61, 1999); (4) least absolute shrinkage and selection (described in R. Tibshirani, "Regression shrinkage and selection via the lasso," J. R. Stat. Soc. Ser. B (Method.), vol. 58, no. 1, pp. 267-88, 1996); (5) focal under-determined system solver (FOCUSS) (described in I. Gorodnitsky and B. Rao, "Sparse signal reconstruction from limited data using FOCUSS: A re-weighted minimum norm algorithm," IEEE Trans. Signal Process., vol. 45, no. 3, pp. 600-16, 1997); and (6) sparse Bayesian learning (described in D. P. Wipf and B. D. Rao, "Sparse Bayesian learning for basis selection," IEEE Trans. Signal Process., vol. 52, no. 8, pp. 2153-64, 2004). All of the above-referenced disclosures are incorporated by reference herein.

Application to EEG Artifact Removal

Figure 1:
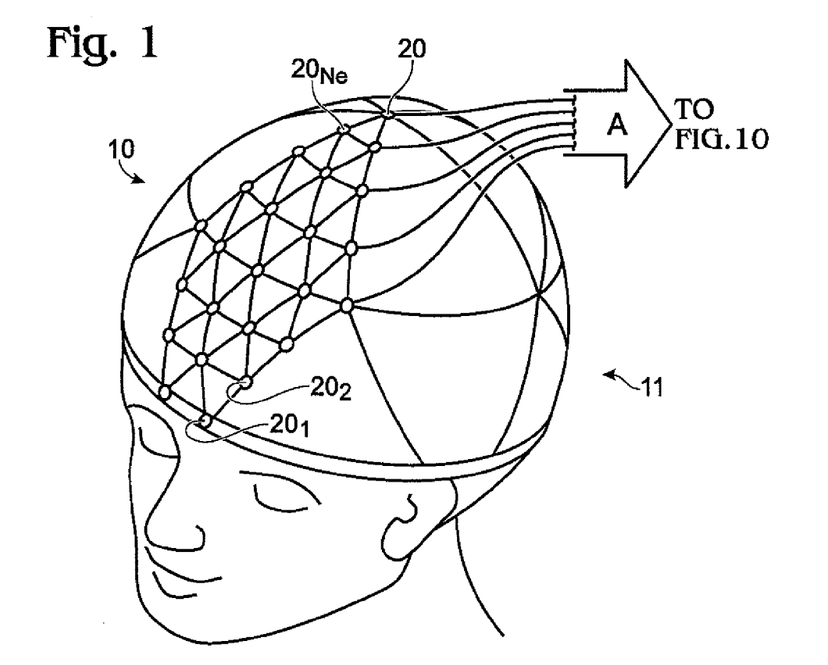
FIG. 1 is pictorial illustration of network of sensors for measuring electrical potentials disposed on a human head as is typical in the prior art for measuring an EEG.

FIG. 1 shows a human head 11 on the scalp surface of which is disposed a network 10 of electrodes 20, namely, $20_1$, $20_2$, ... $20_{Ne}$, or $20_{ke}$, ke ranging from 1 to Ne. The electrodes 20 are adapted to sense respective electrical potentials J, namely $J_1, J_2, \ldots J_{ne}$ (not shown). The electrical potentials J are transmitted to a computer system 30 described below and shown in FIG. 9 (see open arrow "A" in both Figures).

The electrical potentials J are generated by a plurality of sources S inside the skull (not shown) of the head, namely, $S_1$, $S_2, \ldots S_{Ns}$, or $S_{ks}$, ranging from 1 to Ns.

The sources cause, as their effect on the scalp surface, the measured electrical potentials J, defining the following "forward problem:"

$$\begin{bmatrix} S_1 \\ S_2 \\ \vdots \\ S_{Ns} \end{bmatrix} = \begin{bmatrix} K_{1,1} & K_{1,2} & \cdots & K_{1,Ne} \\ K_{2,1} & K_{2,2} & \cdots & K_{2,Ne} \\ \cdots & & & \\ K_{Ns,1} & K_{Ns,2} & \cdots & K_{Ns,Ne} \end{bmatrix} \begin{bmatrix} J_1 \\ J_2 \\ \vdots \\ J_{Ne} \end{bmatrix}$$

or, $$S = KJ,$$

where S defines the outputs of the (Ns) sources S; J defines the (Ne) electrode potentials, or the number of "channels" in the EEG; and the propagation matrix K specifies how electromagnetic energy produced by the sources S propagates through the head to the electrodes 20.

The propagation matrix K is generally constructed by use of simplified models of the head, e.g., concentric spheres corresponding to homogenous portions of grey matter, white matter, cerebrospinal fluid, and skull with idealized conductive properties, but may be based to varying degrees on improvements to such models based on anatomical information such as may be obtained in MRI.

The traditional "inverse problem" is to find an optimum set S that when transformed by an assumed propagation matrix K fits the data J. The traditional ways of solving this problem are well known and need not be described here. Once the solution is found, the equation can be expressed as:

$$TS=J$$

Previously, it was stated that the electrical potentials J are generated by a plurality of sources S inside the skull. That was a simplifying assumption. In fact, sources of electromagnetic energy outside the skull contribute to the measured potentials J, i.e., generally, $J=J_{uncontaminated}+J_{artifact}$:

$$\begin{bmatrix} J_{uncontaminated1} + J_{artifact1} \\ J_{uncontaminated2} + J_{artifact2} \\ \vdots \\ J_{uncontaminatedNd} + J_{artifactNd} \end{bmatrix}$$

This is the problem to which the present invention is directed, to extract $J_{artifact}$ from J so as to leave $J_{uncontaminated}$.

It is recognized that S contains intracranial (inside the skull) sources $S_{intracranial}$ and extracranial (outside the skull) sources $S_{extracranial}$, with $S_{intracranial}$ corresponding to and being responsible for producing $J_{uncontaminated}$, and $S_{extracranial}$ corresponding to and being responsible for producing $J_{artifact}$. According to the invention, it is desired to solve for $J_{uncontaminated}$ using sparse coding.

To illustrate the preferred approach, consider a simple example of representing a single measured signal or channel J with a sparse vector a determined by use of a three atom dictionary $\Phi$.

Figure 2:
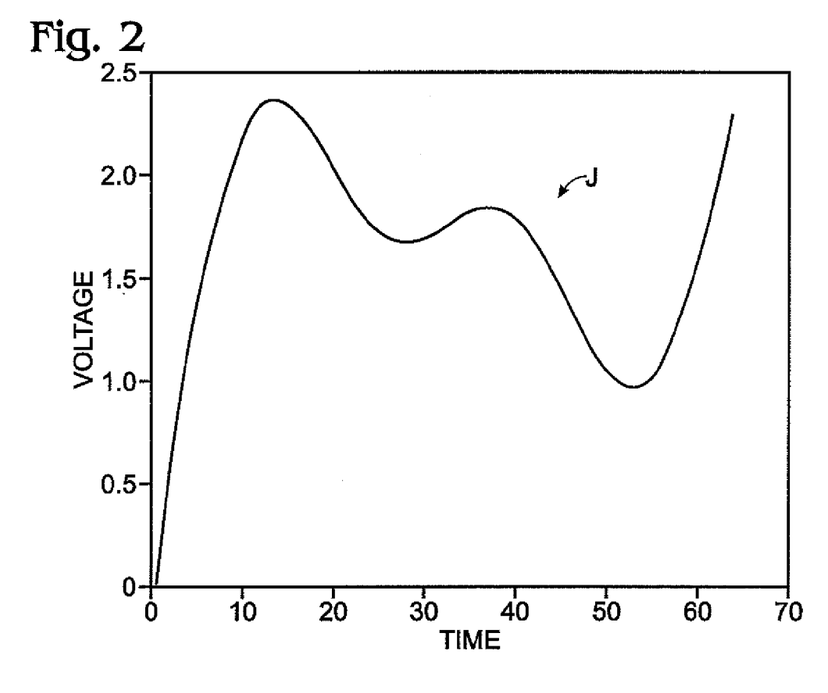
FIG. 2 is a plot of potential in microvolts versus time in milliseconds for a hypothetical signal.

The measured signal J is shown in FIG. 2, and the objective is to resolve it into "good" and "bad" components, i.e., $J_{uncontaminated}$ and $J_{artifact}$.

Figure 3:
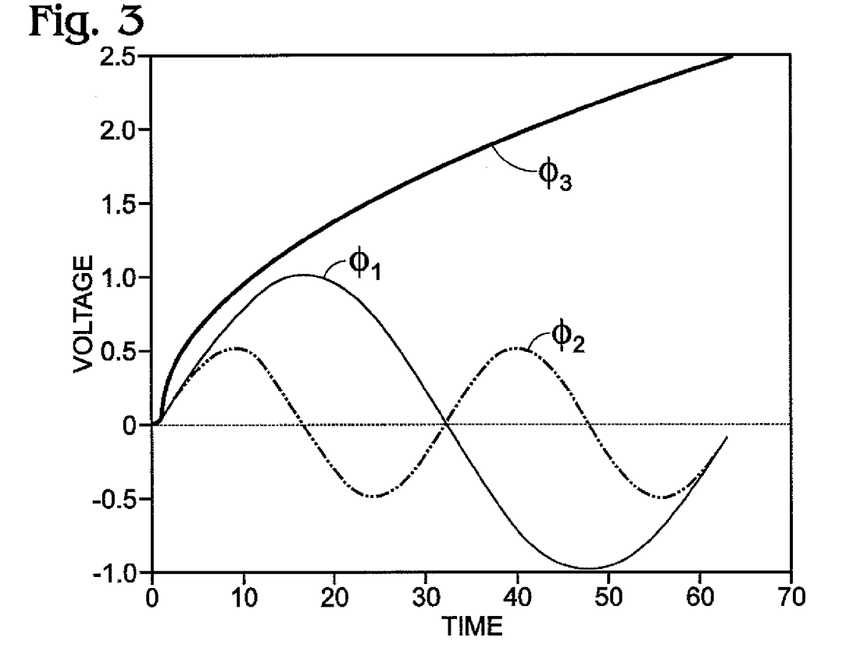
FIG. 3 is a plot of potential versus time for three atoms of a dictionary, with units corresponding to those of FIG. 2, for use in a sparse coding methodology for removing one or more artifacts from the signal of FIG. 2 according to the invention.

The three atoms of the dictionary $\Phi$ are shown in FIG. 3. Since J is a function of time, $\Phi$ are also functions of time. The atoms $\Phi_1$ and $\Phi_2$ are selected to be appropriate Fourier components of the expected, desired signal $J_{uncontaminated}$ due to intracranial sources, and the atom $\Phi_2$ is selected to be an appropriate component for the expected artifactual signal $J_{artifact}$, due to extracranial sources. So there are two "good" atoms $\Phi_1$, $\Phi_2$, and one "bad" atom $\Phi_3$.

As a first alternative, knowing that only the two atoms $a_1$ and $a_2$ are "good" and therefore appropriate for representing $J_{uncontaminated}$, J could be represented as follows:

$$J = [\Phi_1 \quad \Phi_2 \quad 0] \begin{bmatrix} a_1 \\ a_2 \\ a_3 \end{bmatrix}$$

Figure 4:
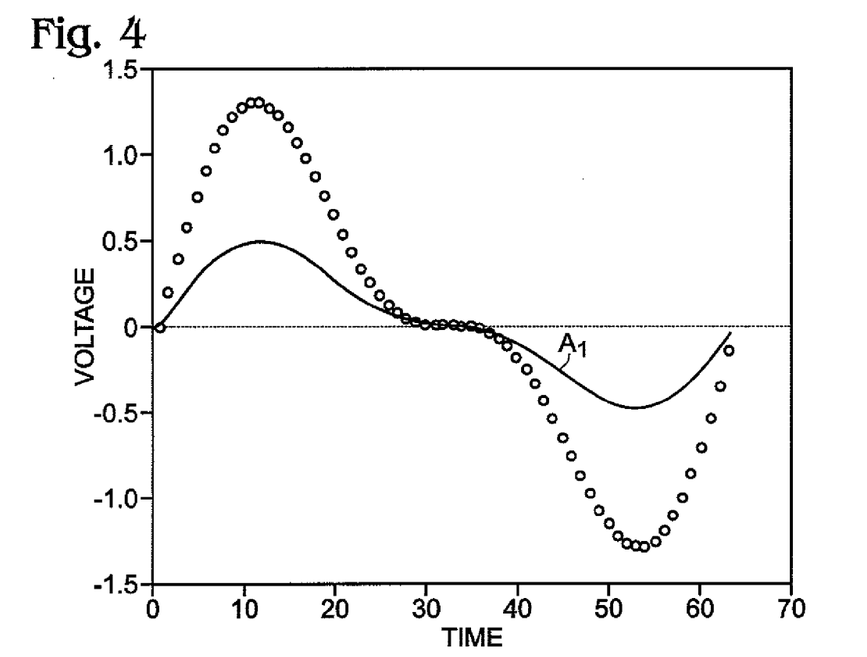
FIG. 4 is a plot of potential versus time for an uncontaminated portion of the signal of FIG. 2, obtained by use of the dictionary of FIG. 3 to solve for a sparse vector according to a first basic methodology according to the invention, and also showing for comparison a known true representation of the uncontaminated portion of the signal represented by a series of circular markings.

We could solve for the sparse vector a and, because it is based only on good atoms, take that as a direct solution for $J_{uncontaminated}$. FIG. 4 shows a sparse coding solution "$A_1$" for $J_{uncontaminated}$, with the true uncontaminated signal being indicated with a sequence of circular markings for comparison.

As a second alternative, J could be represented by using only the "bad" atoms:

$$J = [0 \quad 0 \quad \Phi_3] \begin{bmatrix} a_1 \\ a_2 \\ a_3 \end{bmatrix}$$

In this case we could solve for the sparse vector a and, because it is based only on "bad" atoms, take that as a solution for $J_{artifact}$ and subtract this from J to obtain $J_{uncontaminated}$.

Figure 5:
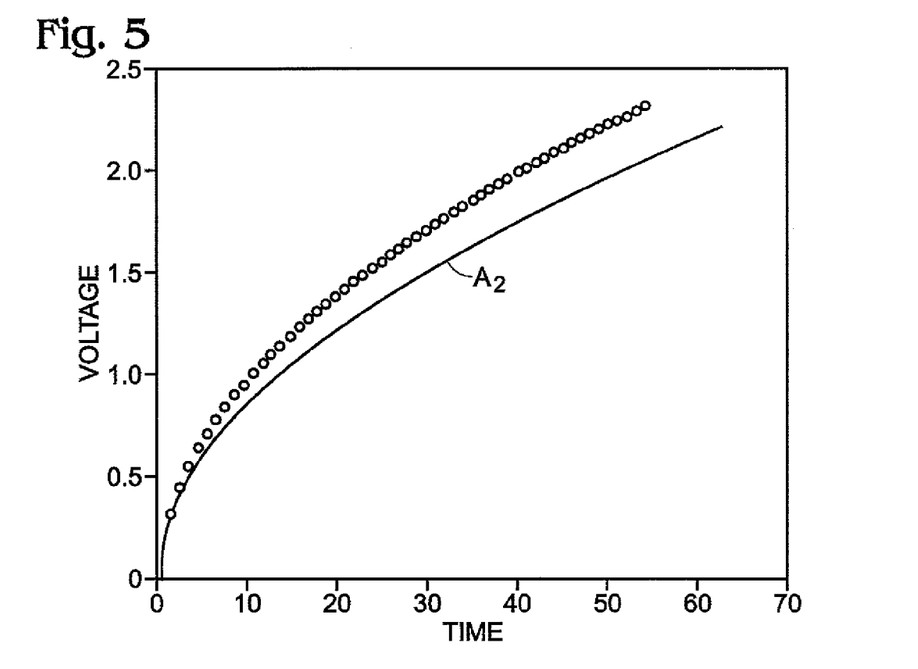
FIG. 5 is a plot of potential versus time for an artifactual portion of the signal of FIG. 2, obtained by use of the dictionary of FIG. 3 to solve for a sparse vector according to a second basic methodology according to the invention, and also showing for comparison a known true representation of the artifactual portion of the signal represented by a series of circular markings.
Figure 6:
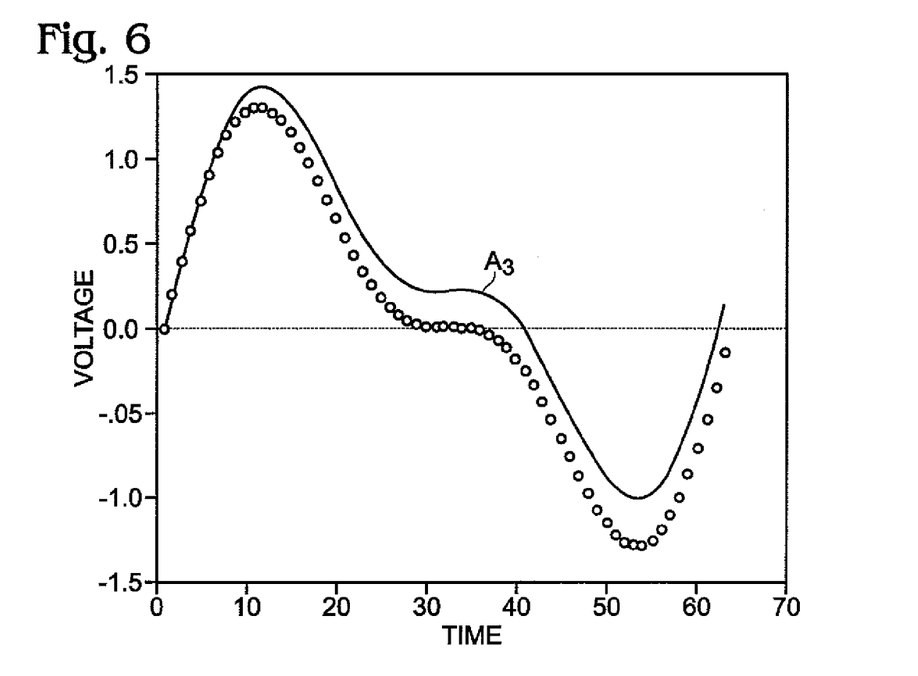
FIG. 6 is a plot of potential versus time for an uncontaminated portion of the signal of FIG. 2, obtained by use of the dictionary of FIG. 3 to solve for a sparse vector according to a third basic methodology according to the invention, and also showing for comparison a known true representation of the uncontaminated portion of the signal represented by a series of circular markings.

FIG. 5 shows a sparse coding solution "$A_2$" for $J_{artifact}$, and FIG. 6 shows the result "$A_3$" for $J_{uncontaminated}$ obtained by subtracting $A_2$ from J, with the true signals $J_{artifact}$ and $J_{uncontaminated}$ being indicated in FIGS. 5 and 6 respectively with a sequence of circular markings for comparison. In this example, the result $A_3$ happens to be better than for the result $A_1$ from the previous example, but that is not a general result.

It is recognized, however, that neither the first nor second alternatives will produce as accurate a representation of $J_{uncontaminated}$ as can be obtained by representing J with all of the atoms, i.e., both the "good" and the "bad" atoms, as follows:

$$J = [\Phi_1 \quad \Phi_2 \quad \Phi_3] \begin{bmatrix} a_1 \\ a_2 \\ a_3 \end{bmatrix}$$

Figure 7:
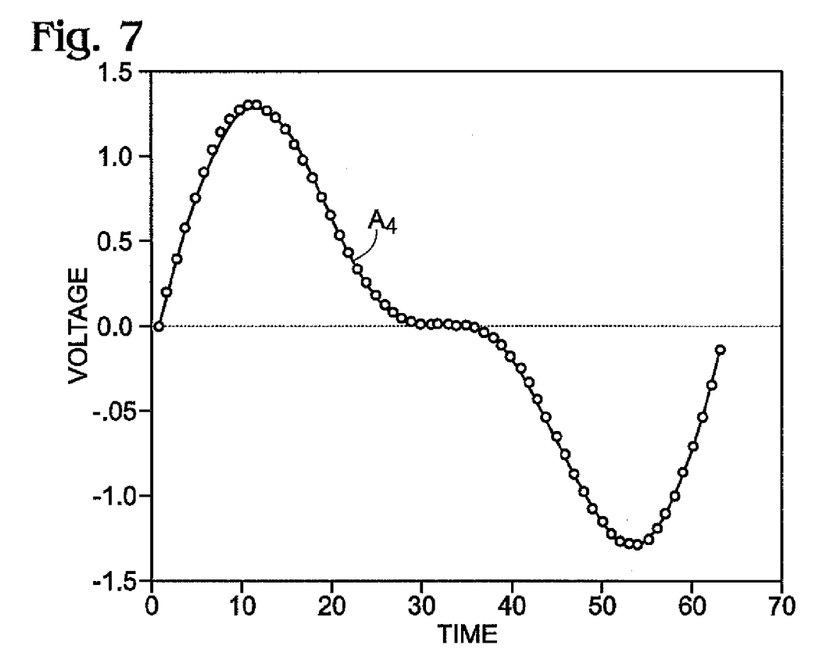
FIG. 7 is a plot of potential versus time for an uncontaminated portion of the signal of FIG. 2, obtained by use of the dictionary of FIG. 3 to solve for a sparse vector according to a preferred methodology according to the invention, and also showing for comparison a known true representation of the uncontaminated portion of the signal represented by a series of circular markings.
Figure 8:
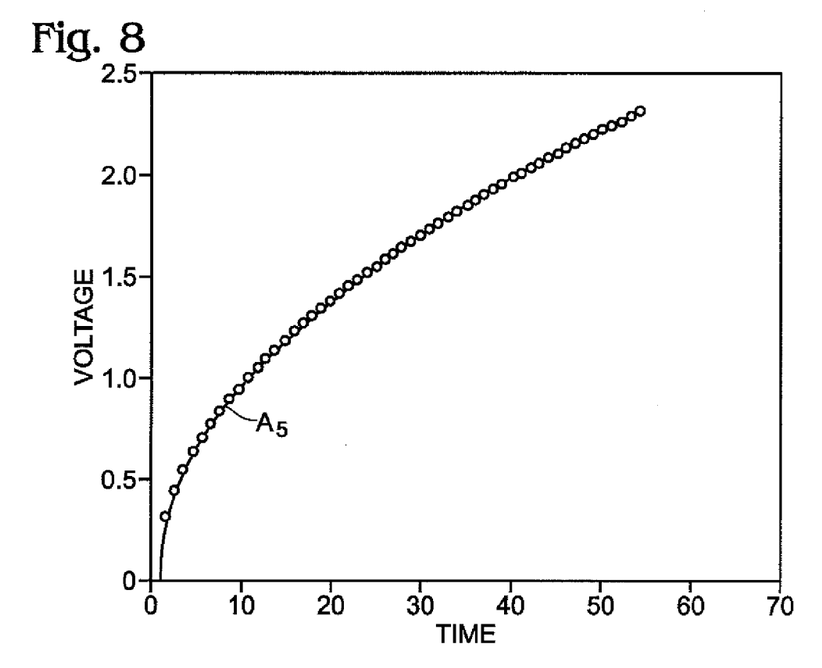
FIG. 8 is a plot of potential versus time for an uncontaminated portion of the signal of FIG. 2, obtained by use of the dictionary of FIG. 3 to solve for a sparse vector according to the preferred methodology used to obtain the results plotted in FIG. 7, and also showing for comparison a known true representation of the uncontaminated portion of the signal represented by a series of circular markings.

FIGS. 7 and 8 show sparse coding solutions "$A_4$" and "$A_5$" for $J_{uncontaminated}$ and $J_{artifact}$ respectively, for comparison with the solutions shown in FIGS. 4 and 6. Once again, the true signals $J_{artifact}$ and $J_{uncontaminated}$ are indicated in the respective Figures with a sequence of circular markings for comparison. The improvement is readily apparent.

To provide the desired dictionary $\Phi$ according to the invention, a lead forward matrix for intracranial sources LFMi is defined for which:

LFMi $S_{intracranial} = J_{uncontaminated}$

The lead forward matrix LFMi defines that portion of the measured potentials J that are due to intracranial sources, i.e., the sources of interest. It can be written as:

$$\begin{bmatrix} LFMi_{1,1} & LFMi_{1,2} & \ldots & \ldots & \ldots & LFMi_{1,Nsi} \\ LFMi_{2,1} & LFMi_{2,2} & \ldots & \ldots & \ldots & LFMi_{2,Nsi} \\ \vdots & & & \ldots & & \\ LFMi_{Ne,1} & LFMi_{Ne,2} & \ldots & \ldots & \ldots & LFMi_{Ne,Nsi} \end{bmatrix}$$

Second, a lead forward matrix for extracranial sources LFMe is defined for which:

LFMe $S_{extracranial} = J_{artifact}$

The lead forward matrix LFMe defines that portion of the measured potentials J that are due to extracranial sources and are therefore artifactual. It can be written as:

$$\begin{bmatrix} LFMe_{1,1} & LFMe_{1,2} & \ldots & \ldots & \ldots & LFMe_{1,Nse} \\ LFMe_{2,1} & LFMe_{2,2} & \ldots & \ldots & \ldots & LFMe_{2,Nse} \\ \vdots & & & \ldots & & \\ LFMe_{Ne,1} & LFMe_{Ne,2} & \ldots & \ldots & \ldots & LFMe_{Ne,Nse} \end{bmatrix}$$

The number of rows of both LFMi and LFMe is equal to the number (Ne) of electrodes 20. The number of columns of LFMi is equal to the number (Nsi) of intracranial sources $S_{intracranial}$, and the number of columns of LFMe is equal to the number (Nse) of extracranial sources $S_{extracranial}$.

The matrices LFMi and LFMe are combined according to the invention to form a coupled lead forward matrix LFMi-LFMe by concatenating the matrices LFMi and LFMe as follows:

$$\begin{bmatrix} LFMi_{1,1} & LFMi_{1,2} & \ldots & \ldots & \ldots & LFMi_{1,Nsi} & LFMe_{1,1} & LFMe_{1,2} & \ldots & \ldots & \ldots & LFMe_{1,Nse} \\ LFMi_{2,1} & LFMi_{2,2} & \ldots & \ldots & \ldots & LFMi_{2,Nsi} & LFMe_{2,1} & LFMe_{2,2} & \ldots & \ldots & \ldots & LFMe_{2,Nse} \\ \vdots & & & \ldots & & & & & & & & \\ LFMi_{Ne,1} & LFMi_{Ne,2} & \ldots & \ldots & \ldots & LFMi_{Ne,Nsi} & LFMe_{Ne,1} & LFMe_{Ne,2} & \ldots & \ldots & \ldots & LFMe_{Ne,Nse} \end{bmatrix}$$

That is, the coupled matrix LFMi-LFMe comprises elements $LFMi_{i,j}$-$LFMe_{i,j'}$; i ranging from 1 to Ne; j ranging from 1 to Nsi; and j' ranging from to Nse.

According to the invention, the coupled matrix LFMi-LFMe is a dictionary $\Phi$, with each column being an atom, or template, for specifying, in linear combination with other atoms of the dictionary, the measured potentials J, i.e.:

$$J = \Phi a$$

In the dictionary $\Phi$ there are Ne rows and Nsi+Nse columns, and it is ensured according to the invention that Nsi+Nse>Ne so that the dictionary is overcomplete and therefore useful as a basis for finding a sparse vector a conforming to the measured potentials defined in J.

It will be noted that the LFMi associated columns Nsi are the "good" atoms analogous to $\Phi_1$ and $\Phi_2$ of the simple example above, and the LFMe associated columns Nse are the "bad" atoms analogous to $\Phi_3$.

The sparse vector a may be found by any of the techniques known in the art of sparse coding. Once the sparse vector is found, it can be used to obtain decoupled results for $J_{uncontaminated}$ and $J_{artifact}$ like those shown in FIGS. 7 and 8 for the three atom dictionary example above.

Following that example, the sparse vector a is [$a_1$ $a_2$ $a_3$], and the dictionary $\Phi$ is [$\Phi_1$ $\Phi_2$ $\Phi_3$], with $\Phi_1$ and $\Phi_2$ being "good" atoms, and $\Phi_3$ being a "bad" atom. To solve for $J_{uncontaminated}$, the "bad" atom $\Phi_3$ can be nullified in the dictionary, e.g., the dictionary can be taken to be [$\Phi_1$ $\Phi_2$ 0]. Then, $$J_{uncontaminated} = [\Phi_1 \quad \Phi_2 \quad 0] \begin{bmatrix} a_1 \\ a_2 \\ a_3 \end{bmatrix} = (\Phi_1 \times a_1) + (\Phi_2 \times a_2)$$

Equivalently, the coefficient $a_3$ could be nullified in the sparse vector, so that:

$$J_{uncontaminated} = [\Phi_1 \quad \Phi_2 \quad \Phi_3] \begin{bmatrix} a_1 \\ a_2 \end{bmatrix}$$

Also equivalently, $\Phi_3$ and $a_3$ can be eliminated from the dictionary and sparse vector respectively, so that:

$$J_{uncontaminated} = [\Phi_1 \quad \Phi_2] \begin{bmatrix} a_1 \\ a_2 \end{bmatrix}$$

This last formulation emphasizes the reduction in dimensionality.

Analogous methods are used to solve for $J_{artifact}$ e.g.:

$$J_{artifact} = \begin{bmatrix} 0 & 0 & \Phi_3 \end{bmatrix} \begin{bmatrix} a_1 \\ a_2 \\ a_3 \end{bmatrix}$$

Or, $$J_{artifact} = \begin{bmatrix} \Phi_1 & \Phi_2 & \Phi_3 \end{bmatrix} \begin{bmatrix} 0 \\ 0 \\ a_3 \end{bmatrix} = \Phi_3 \ X \ a_3$$

Figure 9:
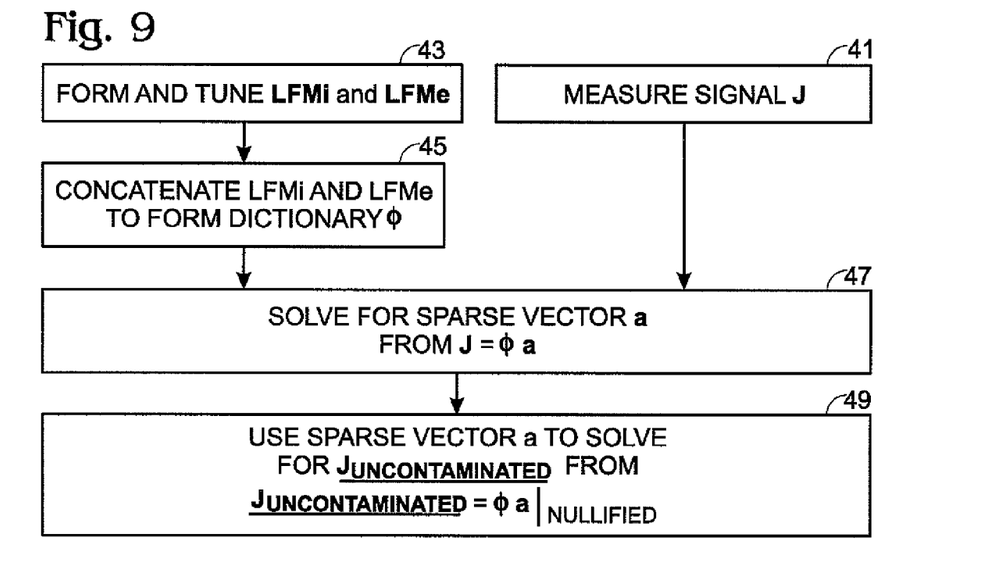
FIG. 9 is a flow chart of a preferred method for separating signal sources by use of physically unique dictionary elements according to the invention.

FIG. 9 is a flow chart summarizing a preferred method referenced as 40. In a step 41 of the method, a measurement is made of the signal J. The signal J is represented by one or more independently measured signal portions or "channels." For example, each of the sensors $20_{ke}$, ke ranging from 1 to Ne as described previously defines a channel of the signal J.

In another step 43 which may be performed at any time relative to stop 41, the matrices LFMi and LFMe are formed and tuned, preferably simultaneously. These matrices are formed of templates corresponding, respectively, to one of the two signal components $J_{uncontaminated}$ and $J_{artifact}$. The matrix LFMe can be initialized using a general template, such as a BCGa template, and both matrices LFMe and LFMi can be tuned by use of well known dictionary learning algorithms using EEG data for a particular individual.

In step 45, the matrices LFMi and LFMe are concatenated to form the coupled dictionary $\Phi$.

In step 47 the dictionary $\Phi$ and the signal J are used to solve for a vector a from the matrix equation J=$\Phi$a. This step preferably includes imposing a constraint that prefers solutions a tending to maximize the sparseness of the coefficients of a, so that a is a sparse vector, though it may be sub-optimal as explained above.

In step 49, the vector a is used to solve for $J_{uncontaminated}$ from the matrix equation $J_{uncontaminated}$=$\Phi$a, with either or both $\Phi$ and a being nullified with respect to templates and coefficients respectively that relate $J_{artifact}$.

The matrices LFMi (intracranial sources) and LFMe (extracranial sources) can be constructed using standard techniques. Preferably, LMFi is constructed by use of (1) head tissue segmentation and cortex surface extraction using MRI or CT images; (2) cortex surface tessellation and dipole placement; (3) head tissue conductivity estimation using bounded electrical impedance tomography; (4) dipole-to-sensor alignment using Photometry; and (5) finite difference calculation of LFMi based on the results of steps (1)-(4).

LFMe is typically obtained by acquiring EEG waveforms characteristic of the extracranial source activity, and generating a number of different templates for use as "atoms" in the dictionary $\Phi$ based on these characteristic waveforms by use of standard techniques such as averaging, grouping, and adaptive learning.

It is recognized as being important that the intracranial sources produce a component ($J_{uncontaminated}$) of the signal J that can be clearly distinguished from the artifactual component ($J_{artifact}$) produced by the extracranial sources.

More particularly, the uncontaminated signal component is significantly "fuzzier" as a result of having propagated through the skull. The precise measure of the fuzziness is in the spatial frequencies contained in the uncontaminated component of the signal, which are significantly lower than those contained in the artifactual component. The lower spatial frequencies represent a greater amount of spatial "smearing" of the uncontaminated component owing to its interaction with the skull.

Going a step further, the columns of the lead forward matrices LFMi and LFMe are recognized as representing templates of activity which, due to the differences in spatial frequency noted above are unique to the two types of sources. Particularly, in the case of the matrix LFMi, the templates can essentially only arise from intracranial sources, and in the case of the matrix LFMe, the templates can essentially only arise from extracranial sources.

Going yet another step further, it is recognized these templates of activity can be combined to form a coupled dictionary, which can be used as the basis for finding a sparse code that, because there is such a clear dichotomy between the templates associated with the two types of sources, is able to efficiently separate the measured signal J into the corresponding components.

Preferably, the methodology is used to separate signals resulting from two types of sources, where there are distinct differences in the signals resulting from spatial separation of the sources of one type from the sources of the other type, but the methodology could be used to separate signals based on differences resulting from other causes, and the methodology could also be used where there are more than two types of sources.

A signature characteristic of the methodology is that it simultaneously separates the two components, representing a qualitative departure from the standard methodology noted previously. One of the outstanding features of the methodology is that, instead of assuming independent sources as in traditional ICA, it assumes redundant sources to make use of additional information that provides for improved signal modeling and analysis.

Figure 10:
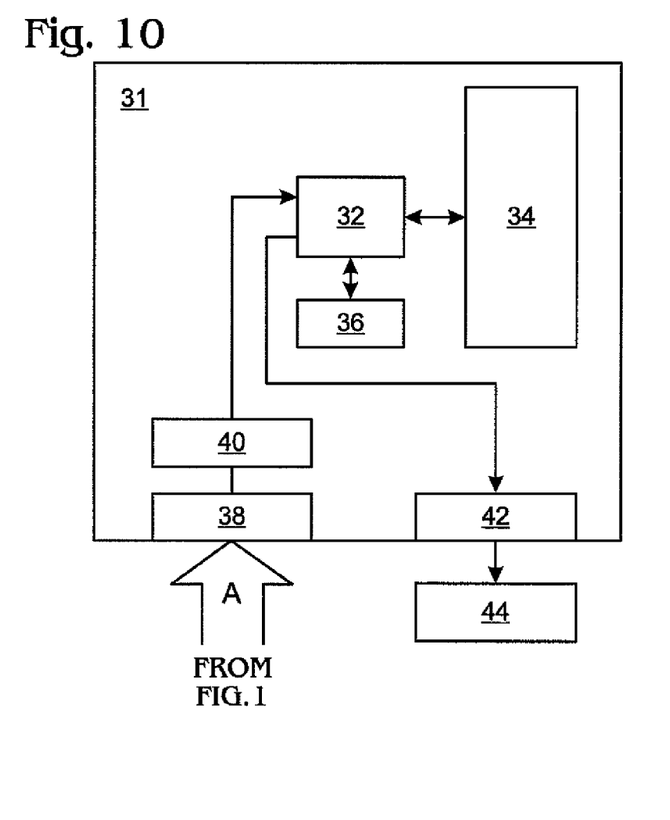
FIG. 10 is a block diagram of a computer system for performing computations necessary for identifying the portions of the signal plotted in FIGS. 4-8.

The computations described are preferably performed on a computer system 30 such as that shown in FIG. 10. The system 30 has a computer 31 which may be a standard PC or Mac, with a processing unit 32, a storage memory 34 for storing data and data processing instructions, a working memory 36 which may be part of the storage memory for performing the stored data processing instructions on the stored data, a data input bus 38 for receiving the data, an analog to digital converter 40 for transforming the data to digital form if the data are not already being presented in digital form, and a data output bus 42 for outputting data processed by the system. From the data output bus 42, the data may be transmitted to another computer system, or to a data rendering device 44 such as a display screen or printer for rendering the data so that the data can be visually perceived.

In particular, the computer system 30 is preferably used to receive the signal J and the dictionary as inputs, solve for the sparse vector a, $J_{uncontaminated}$ and, if desired, $J_{artifact}$, and output the results, for rendering or for use in further computations, which could be carried out in the same computer system or another computer system, either contemporaneously or at a later time.

There may be any number of procedures that are mathematically equivalent to those described herein, and it will be understood that reference, express or implied, to particular mathematical procedures, constructs and definitions, such as matrix algebra, matrices, and columns or rows, are intended to include any and all such equivalent combinations of procedures, constructs and definitions. Similarly, reference to solving an equation such as J=$\Phi$a is intended to include solving any equation that would provide equivalent results.

It will also be understood that, while a specific method for separating signal sources by use of physically unique dictionary elements has been shown and described as preferred, other methodologies could be utilized, in addition to those already mentioned, without departing from the principles of the invention. For example, though the invention is particularly well suited for EEG artifact removal for the reason noted above, it is to be understood that artifact removal may be carried out according to the invention on signals that are not EEG signals, i.e., the methodology has general applicability, such as for MEG and array ultrasound.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for separating two signals components of a signal produced by two distinct types of signal sources, the two types of signal sources being responsible for, respectively, one of the signal components being a desired, uncontaminated signal component and the other of the signal components being an undesired, artifactual signal component, wherein the uncontaminated signal component is caused by neural activity inside the skull of an animal and the artifactual signal component is caused by a source or sources located outside the skull, wherein one of the types of signal sources is spatially separated from the other of the types of signal sources with a result being that the signal component associated with one of the types of signal sources and the signal component associated with the other of the types of signal sources propagate through different conductive paths and thereby have different spatial frequencies, the method comprising:

measuring the signal at one or more locations;

simultaneously separating the two signal components by using a computer to perform steps including forming a first plurality of templates corresponding to one of the signal components, forming a second plurality of templates corresponding to the other signal component, combining the first and second pluralities of templates in a matrix, solving for a vector relating the signal to the sources of both types by use of the matrix, said vector thereby defining coefficients corresponding to both signal components, and computing a representation of the uncontaminated signal component by use of the matrix and vector, the computing step including nullifying at least one of (a) the elements of the vector, and (b) the templates in the matrix, corresponding to the artifactual signal component, and outputting the results, for rendering or for use in further computations.

2. The method of claim 1, further comprising disposing, outside the skull, an array of spaced-apart electrical sensors, wherein said step of measuring includes measuring the signal at multiple locations by receiving electrical outputs produced by the sensors, wherein the uncontaminated signal component contains lower spatial frequencies than the artifactual signal component as a result of having propagated through the skull.

3. The method of claim 2, wherein the sensors are disposed on the surface of the head of the animal.

4. The method of claim 3, further comprising ensuring that the number of templates in the matrix is greater than the number of locations, wherein said step of solving includes imposing a constraint that prefers solutions tending to maximize the sparseness of the coefficients.

5. The method of claim 4, wherein said step of measuring includes measuring the signal at multiple locations.

6. The method of claim 2, further comprising ensuring that the number of templates in the matrix is greater than the number of locations, wherein said step of solving includes imposing a constraint that prefers solutions tending to maximize the sparseness of the coefficients.

7. The method of claim 6, wherein said step of measuring includes measuring the signal at multiple locations.

8. The method of claim 1 further comprising ensuring that the number of templates in the matrix is greater than the number of locations, wherein said step of solving includes imposing a constraint that prefers solutions tending to maximize the sparseness of the coefficients.

9. The method of claim 8, wherein said step of measuring includes measuring the signal at multiple locations.

10. The method of claim 1, wherein said step of measuring includes measuring the signal at multiple locations.

* * * * *